US012387820B2

United States Patent
Gurcan et al.

(10) Patent No.: US 12,387,820 B2
(45) Date of Patent: *Aug. 12, 2025

(54) SYNTHETIC IHC-STAINED DIGITAL SIDES GENERATED USING ARTIFICIAL NEURAL NETWORKS

(71) Applicant: Ohio State Innovation Foundation, Columbus, OH (US)

(72) Inventors: Metin Nafi Gurcan, Winston-Salem, NC (US); Caglar Senaras, Senaras (NL); Gerard Lozanski, West Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/653,527

(22) Filed: May 2, 2024

(65) Prior Publication Data

US 2024/0290433 A1 Aug. 29, 2024

Related U.S. Application Data

(60) Continuation of application No. 18/104,662, filed on Feb. 1, 2023, now Pat. No. 11,978,536, which is a division of application No. 16/271,356, filed on Feb. 8, 2019, now Pat. No. 11,621,058.

(60) Provisional application No. 62/628,027, filed on Feb. 8, 2018.

(51) Int. Cl.
*G16B 40/30* (2019.01)
*G01N 33/50* (2006.01)
*G06N 3/045* (2023.01)
*G06N 3/088* (2023.01)
*G06N 20/20* (2019.01)

(52) U.S. Cl.
CPC ......... *G16B 40/30* (2019.02); *G01N 33/5005* (2013.01); *G06N 3/045* (2023.01); *G06N 3/088* (2013.01); *G06N 20/20* (2019.01)

(58) Field of Classification Search
CPC .... G16B 40/30; G01N 33/5005; G06N 3/045; G06N 3/088; G06N 20/20; G06N 7/01; G06N 3/047; G06N 3/08
See application file for complete search history.

(56) References Cited

U.S. PATENT DOCUMENTS

| | | | | |
|---|---|---|---|---|
| 10,943,186 | B2 * | 3/2021 | Guo | G06K 9/6256 |
| 2014/0270457 | A1 | 9/2014 | Bhargava | |
| 2015/0347702 | A1 | 12/2015 | Chukka | |
| 2017/0249548 | A1 | 8/2017 | Nelson | |

(Continued)

OTHER PUBLICATIONS

Hou, L., Agarwal, A., Samaras, D., Kurc, T. M., Gupta, R. R., & Saltz, J. H. (2017). Unsupervised histopathology image synthesis. arXiv preprint arXiv:1712.05021. (Year: 2017).*

(Continued)

*Primary Examiner* — Andrae S Allison
(74) *Attorney, Agent, or Firm* — Meunier Carlin & Curfman LLC

(57) ABSTRACT

Disclosed herein are systems, methods and computer-program products to create synthetic immunohistochemistry (IHC) stained digital slides generated using artificial neural networks (ANNs). In some implementations, the created digital slides can be used as a ground truth to evaluate a method of analyzing IHC stained tissues.

15 Claims, 9 Drawing Sheets illustrates an exemplary overview system for training and inference phases to create synthetic digital sides;

(56) References Cited

U.S. PATENT DOCUMENTS

| | | | |
|---|---|---|---|
| 2017/0270660 A1 | 9/2017 | Krueger | |
| 2017/0274019 A1 | 9/2017 | Wang | |
| 2017/0298446 A1 | 10/2017 | Byrd | |
| 2019/0087780 A1* | 3/2019 | Cerqueira | G06Q 10/101 |
| 2019/0156476 A1* | 5/2019 | Yoshida | G06V 10/56 |
| 2019/0156481 A1* | 5/2019 | Sekiguchi | G06T 7/74 |
| 2019/0266486 A1* | 8/2019 | Yamada | G06V 20/698 |
| 2019/0347467 A1* | 11/2019 | Ohsaka | G06N 3/08 |
| 2020/0340909 A1* | 10/2020 | Ohsaka | G06N 20/20 |
| 2020/0388028 A1 | 12/2020 | Agus | |
| 2020/0394825 A1* | 12/2020 | Stumpe | G06V 10/82 |
| 2020/0405148 A1* | 12/2020 | Tran | G16H 50/20 |
| 2021/0325308 A1 | 10/2021 | Kannan | |
| 2022/0189150 A1* | 6/2022 | Bentaieb | G16C 20/70 |

OTHER PUBLICATIONS

Senaras C, Niazi MKK, Sahiner B, Pennell MP, Tozbikian G, Lozanski G, et al. (2018) Optimized generation of high-resolution phantom images using cGAN: Application to quantification of Ki67 breast cancer images. PLoS One 13(5): e0196846. https://doi.org/10.1371/journal.pone.0196846 (Year: 2018).*

A. L. Maas, A. Y. Hannun, and A. Y. Ng, "Rectifier nonlinearities improve neural network acoustic models," in Proc. ICML, 2013.

B. B. Cheikh, C. Bor-Angelier, and D. Racoceanu, "A model of tumor architecture and spatial interactions with tumor microenvironment in breast carcinoma," in SPIE Medical Imaging, 2017, pp. 101400C-101400C-8.

C. Szegedy, V. Vanhoucke, S. Ioffe, J. Shlens, and Z. Wojna, "Rethinking the inception architecture for computer vision," in Proceedings of the IEEE Conference on Computer Vision and Pattern Recognition, 2016, pp. 2818-2826.

C. Taylor and R. M. Levenson, "Quantification of immunohistochemistry—issues concerning methods, utility and semiquantitative assessment II," Histopathology, vol. 49, pp. 411-424, 2006.

D. C. Zaha, "Significance of immunohistochemistry in breast cancer," World journal of clinical oncology, vol. 5, p. 382, 2014.

D. Kingma and J. Ba, "Adam: A method for stochastic optimization," arXiv preprint arXiv:1412.6980, 2014.

D. Shen, G. Wu, and H.-I. Suk, "Deep Learning in Medical Image Analysis," Annual Review of Biomedical Engineering, 2017.

I. Goodfellow, J. Pouget-Abadie, M. Mirza, B. Xu, D. Warde-Farley, S. Ozair, et al., "Generative adversarial nets," in Advances in neural information processing systems, 2014, pp. 2672-2680.

J. L. Ba, J. R. Kiros, and G. E. Hinton, "Layer normalization," arXiv preprint arXiv:1607.06450, 2016.

K. Niazi, F. Abas, C. Senaras, M. Pennell, B. Sahiner, W. Chen, et al., "Nuclear IHC enumeration: A digital phantom to evaluate the performance of automated algorithms in digital pathology," PLoS One 2018, 13(5): e0196547.

M. Bojarski, D. Del Testa, D. Dworakowski, B. Firner, B. Flepp, P. Goyal, et al., "End to end learning for self-driving cars," arXiv preprint arXiv:1604.07316, 2016.

M. D. Reid, P. Bagci, N. Ohike, B. Saka, I. E. Seven, N. Dursun, et al., "Calculation of the Ki67 index in pancreatic neuroendocrine tumors: a comparative analysis of four counting methodologies," Modern pathology: an official journal of the United States and Canadian Academy of Pathology, Inc, vol. 28, p. 686, 2015.

M. F. A. Fauzi, M. Pennell, B. Sahiner, W. Chen, A. Shana'ah, J. Hemminger, et al., "Classification of follicular lymphoma: the effect of computer aid on pathologists grading," BMC medical informatics and decision making, vol. 15:115, 2015.

M. K. K. Niazi, E. Downs-Kelly, and M. N. Gurcan, "Hot spot detection for breast cancer in Ki-67 stained slides: image dependent filtering approach," in SPIE Medical Imaging, 2014, 9041, 904106.

M. K. K. Niazi, M. Pennell, C. Elkins, J. Hemminger, M. Jin, S. Kirby, et al., "Entropy based quantification of Ki-67 positive cell images and its evaluation by a reader study," in SPIE Medical Imaging, 2013, 8676, 86760I-1.

M. K. K. Niazi, Y. Lin, F. Liu, A. Ashoka, M. Marcellin, G. Tozbikian, et al., "Pathological image compression for big data image analysis: Application to hotspot detection in breast cancer," Artificial Intelligence In Medicine 95 (2019) 82-87.

O. Ronneberger, P. Fischer, and T. Brox, "U-net: Convolutional networks for biomedical image segmentation," in International Conference on Medical Image Computing and Computer-Assisted Intervention, 2015, pp. 234-241.

P. Isola, J.-Y. Zhu, T. Zhou, and A. A. Efros, "Image-to-image translation with conditional adversarial networks," arXiv preprint arXiv:1611.07004, 2016.

S. Di Cataldo, E. Ficarra, A. Acquaviva, and E. Macii, "Automated segmentation of tissue images for computerized IHC analysis," Computer methods and programs in biomedicine, vol. 100, pp. 1-15, 2010.

S. Ioffe and C. Szegedy, "Batch normalization: Accelerating deep network training by reducing internal covariate shift," arXiv preprint arXiv:1502.03167, 2015.

V. J. Tuominen, S. Ruotoistenmäki, A. Viitanen, M. Jumppanen, and J. Isola, "ImmunoRatio: a publicly available web application for quantitative image analysis of estrogen receptor (ER), progesterone receptor (PR), and Ki-67," Breast cancer research, vol. 12, p. R56, 2010.

X. Wang and A. Gupta, "Generative image modeling using style and structure adversarial networks," in European Conference on Computer Vision, 2016, pp. 318-335.

Caglar Senaras, Berkman Sahiner, Gary Tozbikian, Gerard Lozanski, Metin N. Gurcan, "Creating synthetic digital slides using conditional generative adversarial networks: application to Ki67 staining," Proc. SPIE 10581, Medical Imaging 2018: Digital Pathology, 1058103 (Mar. 6, 2018); (Year: 2018).

Xu, Zidui, Xi Li, Xihan Zhu, Luyang Chen, Yonghong He, and Yupeng Chen. "Effective lmmunohistochemistry Pathology Microscopy Image Generation Using CycleGAN." Frontiers in Molecular Biosciences 7 (2020) (Year: 2020).

Xu, Z., Moro, C. F., Boz6ky, B., and Zhang, Q. (2019). Gan-based virtual restaining: a promising solution for whole slide image analysis. arXiv:1901.04059 (Year: 2019).

J. Tremblay et al., "Training Deep Networks with Synthetic Data: Bridging the Reality Gap by Domain Randomization," 2018 IEEE/CVF Conference on Computer Vision and Pattern Recognition Workshops (CVPRW), 2018, pp. 1082-10828, doi: 10.1109/CVPRW.2018.00143. (Year: 2018).

Ronneberger, Olaf, Philipp Fischer, and Thomas Brox. "U-net: Convolutional networks for biomedical image segmentation." International Conference on Medical image computing and computer-assisted intervention. Springer, Cham, 2015. (Year: 2015).

Senaras, Caglar, et al. "Creating synthetic digital slides using conditional generative adversarial networks: application to Ki67 staining." Medical Imaging 2018: Digital Pathology. vol. 10581. SPIE, 2018. (Year: 2018).

Isola, Phillip, et al. "Image-to-image translation with conditional adversarial networks." Proceedings of the IEEE conference on computer vision and pattern recognition. 2017. (Year: 2017).

Bayramoglu, Neslihan, et al. "Towards virtual H&E staining of hyperspectral lung histology images using conditional generative adversarial networks." Proceedings of the IEEE International Conference on Computer Vision Workshops. 2017. (Year: 2017).

M. Khalid Khan Niazi, Anjali A. Satoskar, Metin N. Gurcan, "An automated method for counting cytotoxic T-cells from CDS stained images of renal biopsies," Proc. SPIE 8676, Medical Imaging 2013: Digital Pathology, 867606 (Mar. 29, 2013); doi: 10.1117/12.2007977 (Year: 2013).

Diem et al, Image analysis for accurately counting CD4+ and CDS+ T cells in human tissue, J Viral Methods. Sep. 15, 2015; 222: 117-121. doi:10.1016/j.jviromet.2015.06.004. (Year: 2015).

* cited by examiner

FIG 1 illustrates an exemplary overview system for training and inference phases to create synthetic digital sides;

illustrates the training of the discriminator, D, network;

SYNTHETIC IHC-STAINED DIGITAL SIDES GENERATED USING ARTIFICIAL NEURAL NETWORKS

CROSS-REFERENCE TO RELATED APPLICATION

This application is a continuation application of U.S. non-provisional application Ser. No. 18/104,662 filed Feb. 1, 2023, issuing as U.S. Pat. No. 11,978,536 on May 7, 2024, which is a divisional application of U.S. non-provisional application Ser. No. 16/271,356 filed Feb. 8, 2019, which claims priority to and benefit of U.S. provisional patent application Ser. No. 62/628,027 filed Feb. 8, 2018, each of which are fully incorporated by reference and made a part hereof.

GOVERNMENT SUPPORT CLAUSE

This invention was made with government support under grant number CA134451 awarded by the National Institutes of Health. The government has certain rights in the invention.

BACKGROUND

Field of the Invention

Described herein are systems and methods for generation of in-silico slide images that contain an exact known number of true positive cells, true negative cells, and background representations in a variety of synthesized sample conditions and the use thereof.

Background

Immunohistochemistry (IHC) is widely used in clinical practice to localize specific epitopes of molecules in cells and tissues that aid in diagnosis and prognosis of cancer. It also plays a vital role in selecting an appropriate systemic therapy for cancer patients. Typically, IHC markers are used according to specific guidelines where the intensity of stains and the number of positive cells are expressed as a percentage of all malignant cells. In clinical practice, IHC stain interpretation is often carried out manually. It consists of counting each positively- and negatively-stained cell under the microscope and reporting the ratio of number of positively stained nuclei to the total number of nuclei. Faced with this daunting task and because of the shortage of time, some pathologists revert to estimating the number of cells. As expected, the manual enumeration suffers from poor reproducibility even in the hands of expert pathologists.

A traditional approach for the evaluation of quantitative image analysis methods includes having an expert diligently generate a reference standard (e.g., by segmenting structures or by counting cells), and then comparing the computer results to the reference standard. However, due to inter- and intra-observer variability in performing a quantitative task on digital pathology images, a reference standard generated by one expert is often considered inadequate, and multiple experts' interpretation is sought. Involving multiple experts results in a resource-intensive evaluation process and limits the sample size for the evaluation. If the ground truth were known, as in the case of synthetically generated images, the effort for the evaluation would be immensely reduced, and much larger evaluation data sets could be used, reducing the uncertainty inherent due to limited sample sizes.

There have been some previous efforts to develop synthetic histopathological images: Cheikh et al. recently developed a synthetic histological image generation algorithm by modeling tumor architecture and spatial interactions in breast cancer (B. B. Cheikh, C. Bor-Angelier, and D. Racoceanu, "A model of tumor architecture and spatial interactions with tumor microenvironment in breast carcinoma," in SPIE Medical Imaging, 2017, pp. 101400C-101400C-8.) Although the statistical properties of the synthetic images (i.e. the number of tumor patterns, their area and their shape) were similar to those of real images, the models created 'unrealistic' details in the generated synthetic images.

Therefore, systems and methods are desired that create realistic images to match pathologists' expectations that can be used to validate analytical methods.

SUMMARY

Disclosed and described herein are systems and methods for creating phantom digital histopathological slides by an artificial neural network.

In recent years, the convolutional neural networks (CNN) have become a critical workhorse for many different image processing problems. A novel application of the CNN is in Generative Adversarial Networks (GAN) with a goal to "make the output indistinguishable from reality" (P. Isola, J.-Y. Zhu, T. Zhou, and A. A. Efros, "Image-to-image translation with conditional adversarial networks," arXiv preprint arXiv:1611.07004, 2016.) Described herein, a variation of a GAN, termed conditional GAN (cGAN), is used that allows the generation of realistic histopathological images with a fully controlled ground truth. In one aspect, the synthetic IHC image generated can be used for the evaluation of quantitative image analysis methods for IHC slides. The disclosed systems and methods can generate realistic looking positive and negative nuclei with different shape, size, and spatial distributions.

For example, computer-based systems, methods and computer program product are disclosed herein that involve user defined parameters that permit generation of an in-silico image with ability to select inclusion of various types of stains; cells, including overall number of positive and negative cells, mixed populations, altered morphology, and spatial distributions within the image including overlap, etc. The images can also include artifacts that make interpretation difficult such as debris, other tissues, staining inconsistencies, and the like. The disclosed systems and methods result in images that represent real human cells and structures (healthy and diseased), which are assembled from actual patient samples. This allows digital creation of all the procedural, biochemical, structural and anatomical inconsistencies associated with histology that make accurate counting and diagnosis tricky.

In one aspect, an in-silico standard is created that is comprised of a combination of IHC positive and IHC negative (counterstained) cells. This standard is generated by software that uses an ANN, and generates virtual tissue sections with known numbers (total count, percentages, etc.) of positive and negative cells. For example, the proportion can be varied from less than 1% to 100% of positive cells. User inputs, which may include an image, the number of positive and negative cells, size, shape and/or location of positive and negative cells and/or artifacts, and the like. The distribution of positive and negative cells can be adjusted to mimic true histological sections where positive cells can be distributed evenly throughout the tissue or may show focal clustering depending on intention of the operator. A cluster of cells can be comprised of positive cells with different intensities of staining, different patterns of staining, different cell size with cells showing good separation and cells overlapping (to afford challenge of cell segmentation for computer algorithms). This in silico tissue modeling can be used for different tissue types including lymphoma, different types of breast cancer, lung cancer, prostate cancer, etc. For each tumor type phantom tissue can be further complicated by introduction of other objects such as lymphocytes, histiocytes, blood vessels, nerve bundles, fibrotic fibers, and artifacts such as hemorrhage of necrosis. The view of cells can be rendered at high magnification and low magnification.

By generating a series of virtual tissues (phantoms) with different proportions and distribution of positive and negative cells, the exact number of positive and negative cells is known, therefore, it can be used as for at least the following purposes:

1. IHC standard for industry to test computer algorithms for enumeration of IHC stained cells.
2. IHC standards for pathology quality assurance programs such as those administered by the College of American Pathologists (CAP) and similar organizations for programs used to standardize breast cancer pathology, lung cancer pathology, lymphoma pathology, etc.
3. Using standards with different proportions of positive and negative cells, high resolution slides can be printed on glass that can be used for testing with light microscopy and for testing of high resolution slide scanners.
4. Generate three-dimensional (3D) phantoms of tissue with different proportions of negative and positive cells. Using 3D printers, artificial tissue can be printed using a cartridge of collagen, or other matrix, with a positively and negatively stained suspension of cells. Such 3D printed tissue can be used to standardize histology processing of tissue fixation and tissue cutting.
5. Using 3D printer with cartages of collagen or other Matrix and unstained cells with known immunophenotype, one can generate (print) 3D artificial tissues that can be used as standard for tissue fixation, tissue processing, IHC staining using different IHC platforms, image acquisition, and image IHC analysis.

An objective of embodiments described herein is to provide a reliable approach to generate ground truth in the study and analysis of IHC stained tissues. In most study and analysis of IHC stained images, obtaining the ground truth is a major challenge due to various factors such as availability of experts perform annotation, inter and intra reader-variability and limited dataset. Often, ground truths are either generalization of reader consensus or average of readings among multiple readers which may in the end be biased and can be disputed. Embodiments described herein allow virtual images to be generated that mimic IHC stained tissue at various magnification that are composed of exact proportions of positive and negative cells with controlled distribution of stained cells. These virtual tissue images can be used as a standard for IHC quantification for both computer based image analysis methods and quality assurance programs for manual evaluation of IHC stained tissue by pathologists. Virtual IHC stained sections are created with exact known percentage of positive and negative cells and bias that is associated with IHC standards where truth is based on manual counting of positive cells by pathologist is eliminated.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION

Figure 1:
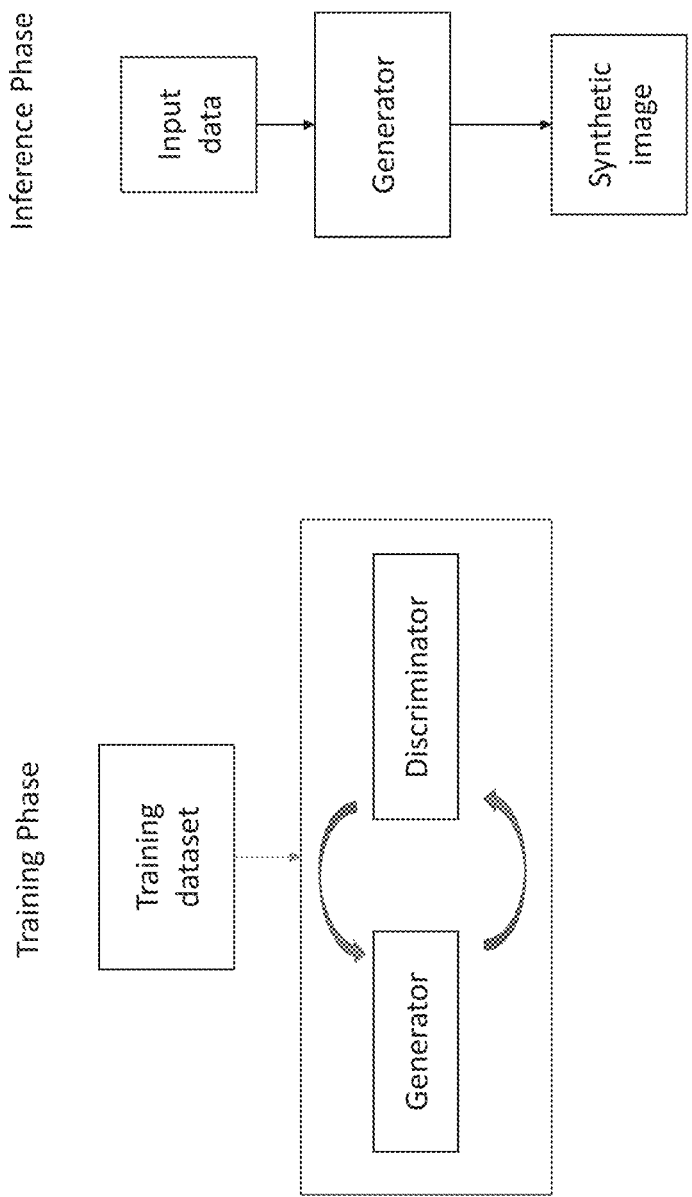
FIG. 1 illustrates an exemplary overview system for training and inference phases to create synthetic digital sides.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The present methods and systems may be understood more readily by reference to the following detailed description of preferred embodiments and the Examples included therein and to the Figures and their previous and following description.

FIG. 1 illustrates an exemplary overview system for creating synthetic digital sides generated using artificial neural networks. Generally, as shown in FIG. 1, the system comprises two main components: a generator, G, and a discriminator, D. A user inputs parameters that are used by the generator to create an output image. For a given real image, $I_r^i$, let $M^i$ represents it corresponding user annotations or segmentation output mask. The generator G, tries to create output images, $I_g^i$, that cannot be distinguished by D from real images. The G is tasked to not only fool D but also to make $I_g^i$ as similar as possible to $I_r^i$. The final objective function is defined as:

$$L_{final} = \arg \min_G \max_D L_{cGAN}(G, D) + L_{l1}(G)$$

where $L_{cGAN}(G, D)$ is part of the objective function which D tries to maximize while learning on how to distinguish real pairs ($M^i$, $I_r^i$) from fake pairs ($M^i$, $I_g^i$). Simultaneously, G tries to minimize $L_{cGAN}(G, D)$ and synthesize fake images that would deceive D. Here, $L_{l1}(G)$ is the difference of output $I_g^i$, and the ground truth, $I_r^i$, as L1 distance.

In an exemplary study, Ki67-stained whole slide images from 32 different breast cancer patients were collected. It is worth mentioning that the proposed method can be easily generalized to other stains (such as CD3, CD4, CD8, CD21, etc.) and diseases (e.g. lung, colon, prostate cancer, kidney disease, etc.). For this particular application, the slides were scanned using an Aperio ScanScope (Leica Biosystems Inc., Buffalo Grove, IL) at 40× magnification where the pixel size is 0.2461×0.2461 µm. An experienced breast pathologist carefully annotated these slides for tumor and non-tumor regions. 84 region-of-interest (ROI) images within the tumor region were randomly selected. Each ROI has a size of 2300×1200 pixels. This size was selected to provide the pathologists with the similar environment when they analyze a slide at 40× magnification under a microscope. Two different input data types were used to train the system: 1) user annotations mask and 2) segmentation output mask.

After the input data generation, all of the ROIs are divided into tiles of size 256×256 pixels. Any tile that doesn't contain a positive or a negative nucleus was excluded from the dataset. There was a total of 684 tiles, 572 of which were used for training, the rest for visual validation.

User annotations mask: To create a training dataset, all of the stain-positive and stain-negative nuclei in the ROIs were marked manually. A stain-positive (or negative) nucleus means that a cell within a tissue is stained positively (or negatively). To ensure the quality of the annotations, four trained operators were used. Each operator first annotated the entire positive and negative nuclei with colored dots in 21 ROIs, analyzed the annotations of another operator, and corrected any annotation mistakes. It is important to mention that the area, orientation or shape information was not saved because the nuclei were represented by only coordinate information represented by dots.

Segmentation output mask: As a second approach, the system was trained with the output of a nuclei segmentation technique that developed in a prior study [M. K. K. Niazi, M. Pennell, C. Elkins, J. Hemminger, M. Jin, S. Kirby, et al., "Entropy based quantification of Ki-67 positive cell images and its evaluation by a reader study," in SPIE Medical Imaging, 2013, pp. 86760I-86760I, which is incorporated by reference]. To illustrate the process, in FIG. 7E, the colors green 702 and red 704 represent the regions that were segmented as positive Ki67 and negative Ki67, respectively. The yellow 706 color was used for lightly stained positive regions, which may occur as staining artifacts or background staining. For each patch, the nuclei segmentation was generated and used it as an input for the cGAN neural network.

Figure 2:
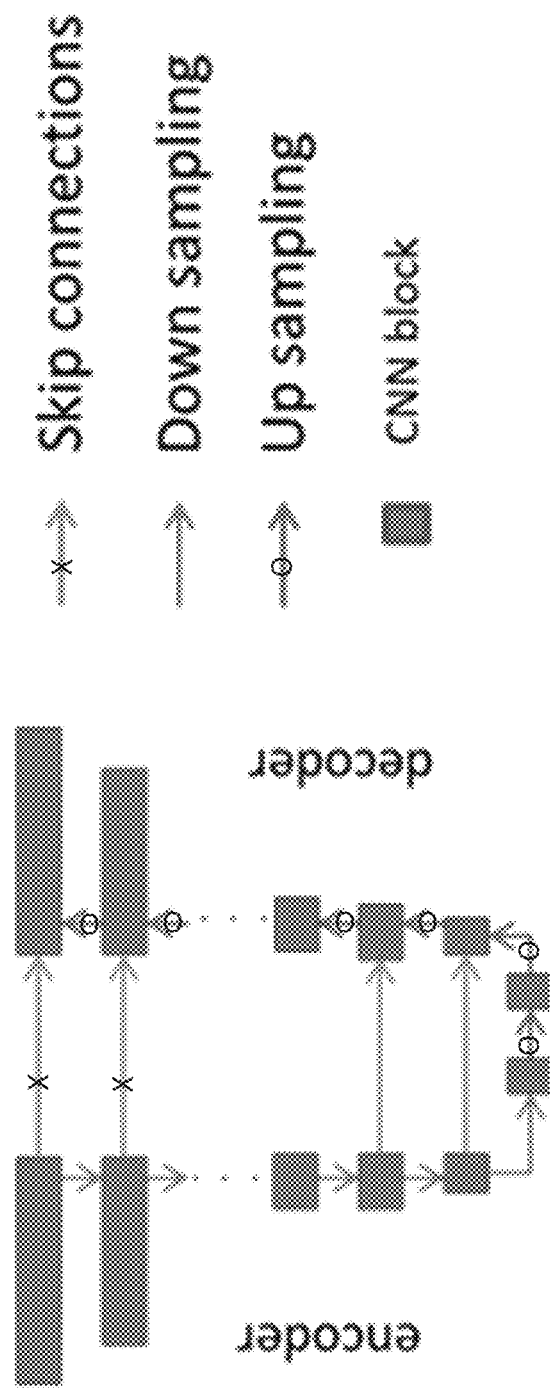
FIG. 2 illustrates a neural network framework for an exemplary generator, G.

In the study, as a generator, G, a modified version of the "U-net" was used [O. Ronneberger, P. Fischer, and T. Brox, "U-net: Convolutional networks for biomedical image segmentation," in International Conference on Medical Image Computing and Computer-Assisted Intervention, 2015, pp. 234-2416, incorporated by reference], whose architectural overview is shown in FIG. 2. All CNN blocks described in FIG. 2 include 3×3 CNNs with 2×2 strides, batch normalization, and leak Relu layers. Instead of batch normalization, the CNN blocks may also include layer normalization. The exemplary generator includes 16 CNN blocks, eight of those are used for encoding and the remaining eight are used for decoding. For larger images, the number of blocks may be increased. The number of filter at $i^{th}$ CNN block, $n_i$, is defined as:

$$n_i = 64 * 2^{min(3,\ L-0.5-|i-L-0.5|)}$$

where L is the number of layers in the encoder and decoder, and is equal to eight in the current setup.

As a discriminator, D, a CNN based classifier "patchGAN" was used [P. Isola, J.-Y. Zhu, T. Zhou, and A. A. Efros, "Image-to-image translation with conditional adversarial networks," arXiv preprint arXiv:1611.07004, 2016, incorporated by reference]. The exemplary classifier includes four CNN blocks and a convolution layer with a 1-dimensional output. In this study, 64×64 patches were used and for each patch; patchGAN tries to identify the input as real or fake. The final output is the average of all responses.

Figure 3:
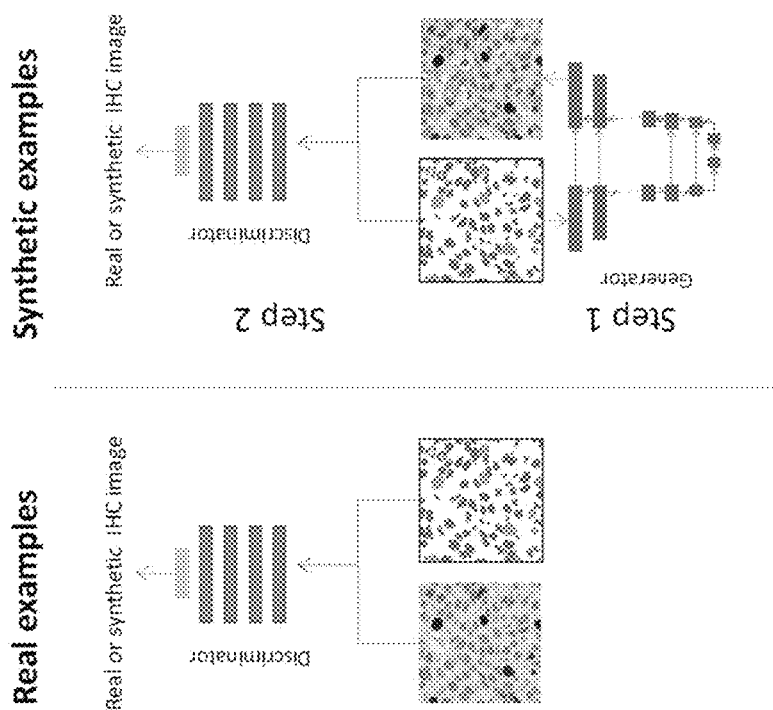
FIG. 3 illustrates the training of the discriminator, D, network.
Figure 4A:
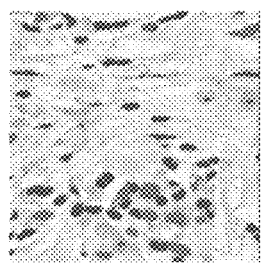
FIGS. 4A-4E are examples of the real and synthetic images used in an exemplary experiment described herein.
Figure 4B:
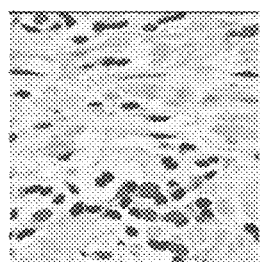
Figure 4C:
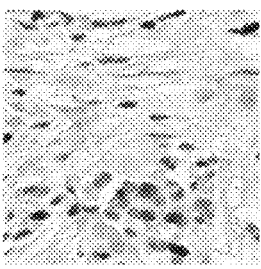
Figure 4D:
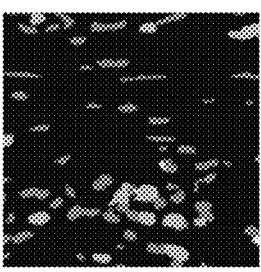
Figure 4E:
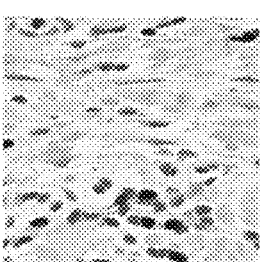

During the training of the proposed method, the standard approach was followed, such that one gradient descent step on D is followed by one gradient descent step on G for optimization. The training procedure for D is given in FIG. 3. The network is optimized with Adam [D. Kingma and J. Ba, "Adam: A method for stochastic optimization," arXiv preprint arXiv: 1412.6980, 2014, incorporated by reference] for 200 epochs with the batch size of four. FIG. 3 illustrates the training of the discriminator, D, network. For real examples, the real images and their segmentation/annotation masks ($M^i$, $I_r^i$) were used as an input. For fake examples, a two-step procedure was applied. In Step 1, we used a generator, G, (U-net) algorithm to create a synthetic image by using the segmentation/annotation. In Step 2, the output of the generator and initial segmentation ($M^i$, $I_g^i$) were used as an input for the discriminator, D.

For inference, the method provides the freedom to manually create a scenario which allows: 1) defining different spatial overlap of nuclei, 2) placement of different sized nuclei at certain locations, 3) and control over spatial frequency of nuclei during synthetic data generation (FIGS. 9A-9H). The input data was fed to the generator, G, and skipped the discriminator, D, to create inferenced synthetic image, i.e. D was not used during validation and testing.

The method was trained for both of the datasets (i.e. "user annotated", and "segmentation output masks") separately. However, the proposed approach may use any manual annotation or another computer segmentation algorithm as an input. Two systems were trained with different input types, and the comparison of their results is presented in the results section, below. The algorithm was tested on an independent set of 122 randomly selected validation images, none of which were used during the training. Each $I_r^i$, and its corresponding $M^i$ were used to create a synthetic image with the same characteristics as $I_r^i$.

In a first experiment, three image analysts and three pathologists were used for their visual evaluations. To maintain the attention of the observers, the experiment was divided into three iterations. In each iteration, each were shown a dataset of 10 images and asked to identify synthetic images. To make the iterations unbiased, the distributions of the synthetic images in the three datasets were kept confidential. The first dataset included 10 synthetic images. The second dataset included 10 real images, and final dataset included five real and five synthetic images.

Reader accuracy in identifying the correct image type (real versus synthetic) was analyzed using a hierarchical Bayesian logistic regression model containing random effects for images and readers. The random reader effects accounted for heterogeneity in reader accuracy while the random image effects accounted for heterogeneity in the difficulty of images. Diffuse or non-informative priors were assigned to all parameters, and the posterior inference was obtained using Metropolis-Hastings sampling run for 500,000 iterations following a 5,000-iteration burn-in. Sampled values were used to calculate the posterior probability that the average reader would be able to identify the correct image type more than 50% of the time if presented with an image of average difficulty. Two readers were excluded from this analysis since their decisions on individual images were not recorded; the number correct and incorrect were just tabulated for each data set. As a secondary analysis, the hierarchical model was extended to included fixed effects of data set to determine if performance differed by ratio of real to artificial cases. Modeling was performed using PROC MCMC in SAS Version 9.4 (SAS Inc, Cary, NC).

To claim that images generated by the described techniques can produce images that can be used for evaluation of computerized quantitative methods, a prerequisite is that the quantitative methods perform similarly for real and synthetic images. To test the disclosed method in a situation similar to the example above, a real data set of 122 Ki-67 stained images was used that was completely independent from the cGAN training data set. This data set is termed as the quantitative comparison dataset below. For each image patch in the quantitative comparison data set, the goal was generating a synthetic image that is different from the real image in terms of its overall appearance (i.e., location and spatial arrangement of the cells) but is similar to the real image in terms of Ki-67 quantitation. To achieve this, a segmentation algorithm [M. K. K. Niazi, M. Pennell, C. Elkins, J. Hemminger, M. Jin, S. Kirby, et al., "Entropy based quantification of Ki-67 positive cell images and its evaluation by a reader study," in SPIE Medical Imaging, 2013, pp. 86760I-86760I, incorporated by reference] was used to generate a segmentation mask, and the segmentation mask and the real image was applied as the input to the cGAN. The output of the cGAN was used as the synthetic image. An example of the real and synthetic images used in this experiment is shown in FIGS. 4A-4E. FIGS. 4A-4E illustrate examples for (FIG. 4A) real image, (FIG. 4B) segmentation result based on the above segmentation algorithm, (FIG. 4C) synthetic image used for evaluation of computerized quantitative method, (FIG. 4D) visual ImmunoRatio output for the real image, and (FIG. 4E) visual ImmunoRatio output for synthetic image.

If the cGAN output is suitable for the evaluation of computerized quantitative methods, then a quantitative method applied to the real and cGAN-generated images should provide similar results, as discussed above. To test this, a quantification method was applied that uses a fundamentally different segmentation algorithm from the above-used segmentation algorithm to both real and synthetic images, termed ImmunoRatio ("M. K. K. Niazi, Y. Lin, F. Liu, A. Ashoka, M. Marcellin, G. Tozbikian, et al., "Interactive Image Compression for Big Data Image Analysis: Application to Hotspot Detection in Breast Cancer," Submitted for Journal publication, 2017, incorporated by reference, which has been accepted to the Journal Artificial Intelligence In Medicine for publication with the same authors "M. Khalid Khan Niazi, Y. Lin, F. Liu, A. Ashok, M. W. Marcellin, G. Tozbikian, M. N. Gurcan, A. Bilgin" but with a slightly different title: "Pathological image compression for big data image analysis: Application to hotspot detection in breast cancer").

Figure 5:
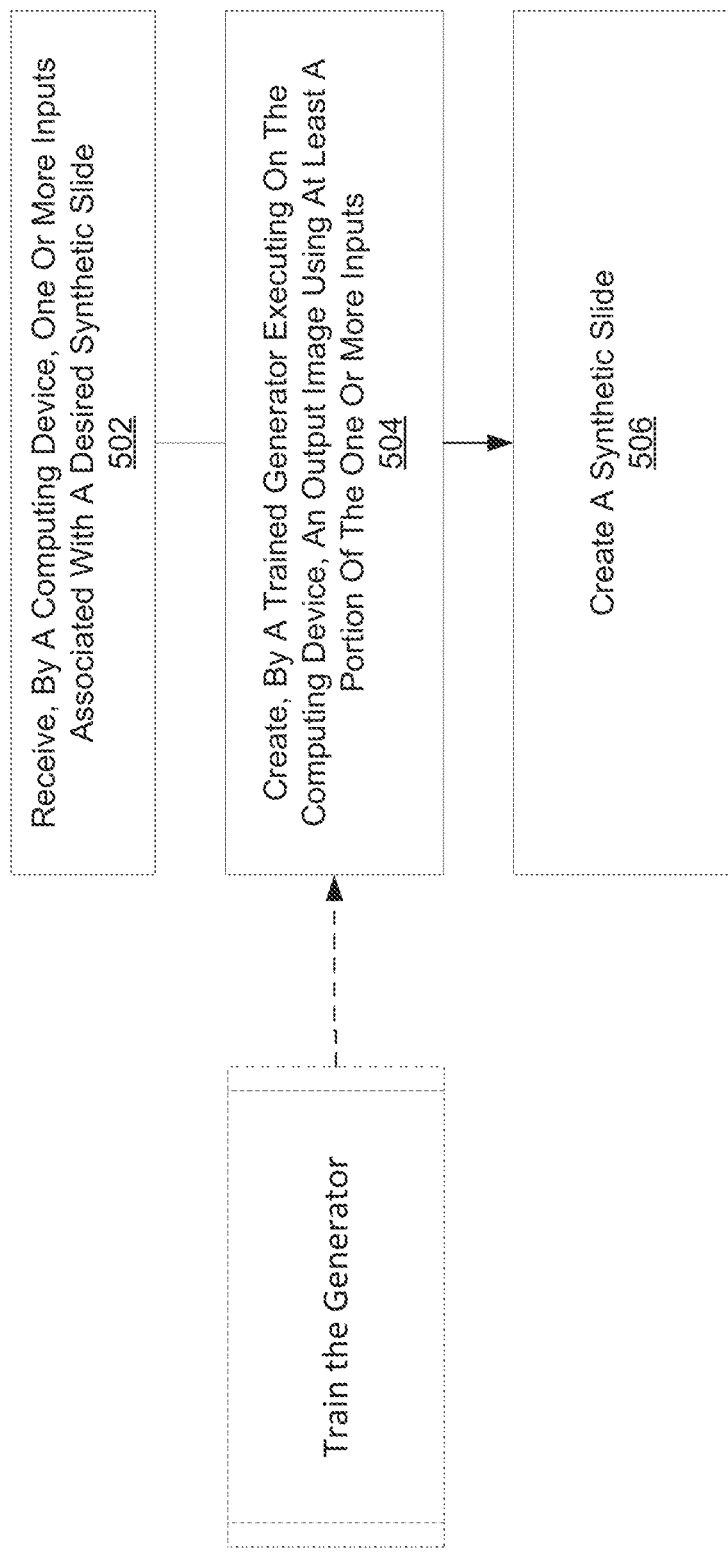
FIG. 5 is a flowchart illustrating the steps of an exemplary method of creating synthetic immunohistochemistry (IHC) stained digital slides generated using artificial neural networks (ANNs)

FIG. 5 is a flowchart that illustrates an exemplary method of creating synthetic digital slides generated using artificial neural networks. In one embodiment, the method comprises 502 receiving, by a computing device, one or more inputs related to the desired synthetic slides. These inputs can be a user annotation or a computer-aided diagnosis (CAD) system's output, an image or a map that contains the location of the positive and negative cells and may include additional information like the orientation and/or size of positive and/or negative cells, the location and type of the artifacts. At 504, at least a portion of the inputs are provided to a trained generator, G, executing on the computing device. During the training, the generator tries to create an image that the discriminator will not able to distinguish from a real image. On the other hand, during training the discriminator learns how to distinguish the fake and real images. The calculated errors are used during the training to update of the weights of the network to improve it. Both the discriminator and the generator are based on neural networks. The trained generator uses artificial neural network (ANN) programming to create an output image. In some instances, the ANN used by the generator comprises convolutional neural networks (CNN). For example, the CNN may be a modified version of the "U-net," as described herein. Finally, at 506 a synthetic slide is created.

The system has been described above as comprised of units. One skilled in the art will appreciate that this is a functional description and that the respective functions can be performed by software, hardware, or a combination of software and hardware. A unit can be software, hardware, or a combination of software and hardware. The units can comprise software for creating synthetic digital slides generated using artificial neural networks. In one exemplary aspect, the units can comprise a computing device that comprises a processor 621 as illustrated in FIG. 6 and described below.

Figure 6:
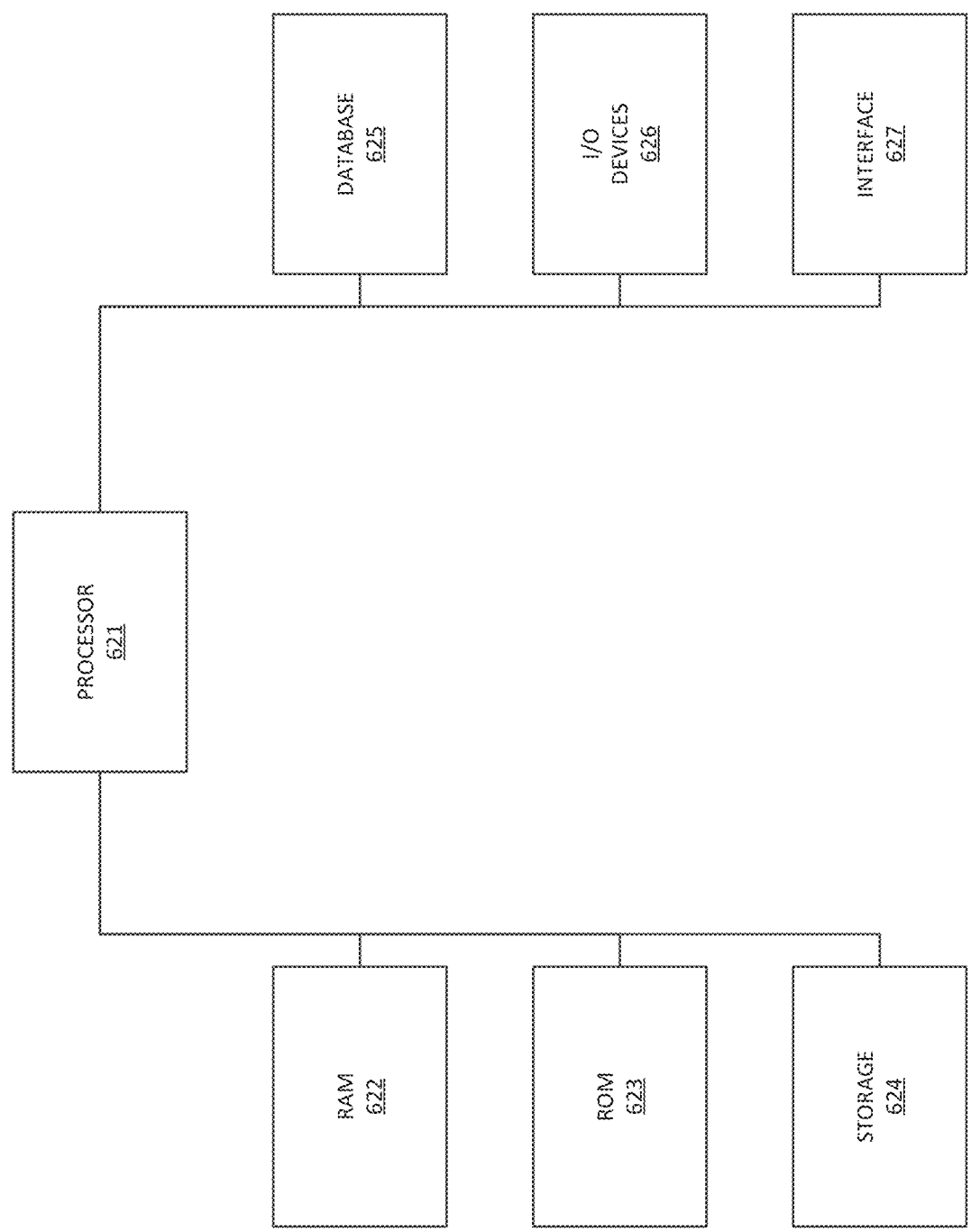
FIG. 6 illustrates an exemplary computer that can be used for creating synthetic immunohistochemistry (IHC) stained digital slides generated using artificial neural networks (ANNs)

FIG. 6 illustrates an exemplary computer that can be used for creating synthetic digital slides generated using artificial neural networks. As used herein, "computer" may include a plurality of computers. The computers may include one or more hardware components such as, for example, a processor 621, a random-access memory (RAM) module 622, a read-only memory (ROM) module 623, a storage 624, a database 625, one or more input/output (I/O) devices 626, and an interface 627. Alternatively, and/or additionally, the computer may include one or more software components such as, for example, a computer-readable medium including computer executable instructions for performing a method associated with the exemplary embodiments. It is contemplated that one or more of the hardware components listed above may be implemented using software. For example, storage 624 may include a software partition associated with one or more other hardware components. It is understood that the components listed above are exemplary only and not intended to be limiting.

Processor 621 may include one or more processors, each configured to execute instructions and process data to perform one or more functions associated with a computer for classifying pathologies of an eardrum based upon one or more images of the eardrum. Processor 621 may be communicatively coupled to RAM 622, ROM 623, storage 624, database 625, I/O devices 626, and interface 627. Processor 621 may be configured to execute sequences of computer program instructions to perform various processes. The computer program instructions may be loaded into RAM 622 for execution by processor 621.

RAM 622 and ROM 623 may each include one or more devices for storing information associated with operation of processor 621. For example, ROM 623 may include a memory device configured to access and store information associated with the computer, including information for identifying, initializing, and monitoring the operation of one or more components and subsystems. RAM 622 may include a memory device for storing data associated with one or more operations of processor 621. For example, ROM 623 may load instructions into RAM 622 for execution by processor 621.

Storage 624 may include any type of mass storage device configured to store information that processor 621 may need to perform processes consistent with the disclosed embodiments. For example, storage 624 may include one or more magnetic and/or optical disk devices, such as hard drives, CD-ROMs, DVD-ROMs, or any other type of mass media device.

Database 625 may include one or more software and/or hardware components that cooperate to store, organize, sort, filter, and/or arrange data used by the computer and/or processor 621. For example, database 625 may store user inputs associated with creating a synthetic slide, store output images from the generator, and store synthetic slides. It is contemplated that database 625 may store additional and/or different information than that listed above.

I/O devices 626 may include one or more components configured to communicate information with a user associated with computer. For example, I/O devices may include a console with an integrated keyboard and mouse to allow a user to maintain a database of synthetic slides, results of the analysis of the output images, metrics, and the like. I/O devices 626 may also include a display including a graphical user interface (GUI) for outputting information on a monitor. I/O devices 626 may also include peripheral devices such as, for example, a printer for printing information associated with the computer, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 627 may include one or more components configured to transmit and receive data via a communication network, such as the Internet, a local area network, a workstation peer-to-peer network, a direct link network, a wireless network, or any other suitable communication platform. For example, interface 627 may include one or more modulators, demodulators, multiplexers, demultiplexers, network communication devices, wireless devices, antennas, modems, and any other type of device configured to enable data communication via a communication network.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process.

Figure 7A:
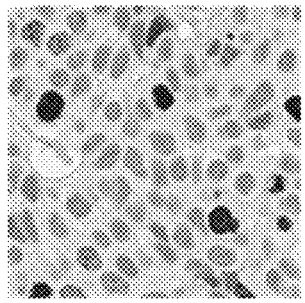
FIGS. 7A-7F illustrates example images and results including annotations and generated synthetic images.
Figure 7B:
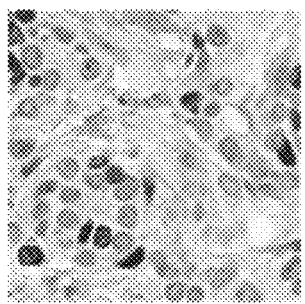
Figure 7C:
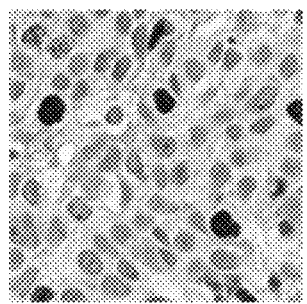
Figure 7D:
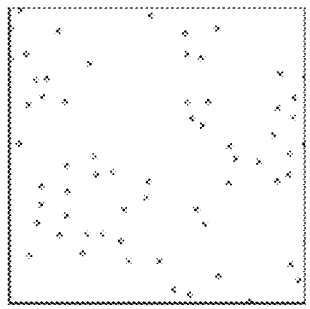
Figure 7E:
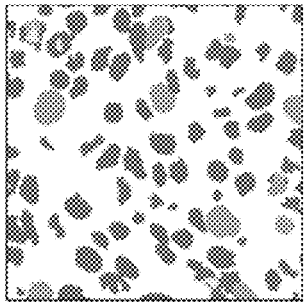
Figure 7F:
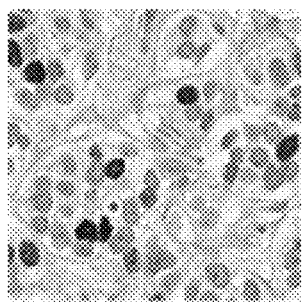

Some example images and results are shown in FIGS. 7A-7F. FIGS. 7A-7F show example images where FIG. 7A is an original image used for annotation; FIG. 7B is a dot based annotation; FIG. 7C is a cGAN generated synthetic image from FIG. 7B; FIG. 7D is an original image used for segmentation; FIG. 7E is a segmentation result using [M. K. K. Niazi, Y. Lin, F. Liu, A. Ashoka, M. Marcellin, G. Tozbikian, et al., "Interactive Image Compression for Big Data Image Analysis: Application to Hotspot Detection in Breast Cancer," Submitted for Journal publication, 2017, incorporated by reference has been accepted to the Journal Artificial Intelligence In Medicine for publication with the same authors "M. Khalid Khan Niazi, Y. Lin, F. Liu, A. Ashok, M. W. Marcellin, G. Tozbikian, M. N. Gurcan, A. Bilgin" but with a slightly different title: "Pathological image compression for big data image analysis: Application to hotspot detection in breast cancer"]; and FIG. 7F is a cGAN generated image from FIG. 7E. FIG. 7B shows the manual nuclei annotations for an example image in FIG. 7A. The output of the generator is given in FIG. 7C. Similarly, the output of the generator by using segmentation algorithm's output (FIG. 7E) is given in FIG. 7F. The numbers of correctly identified real and synthetic image by readers are given in Table 1.

According to a hierarchical logistic regression model, the probability that the average reader would be able to correctly classify an image as synthetic or real more than 50% of the time was only 44.7%. These results suggest that, overall, readers are incapable of distinguishing synthetic images from real ones. However, the results differed by data set: when presented with a data set comprised entirely of real images, the posterior probability of correctly classifying an image more than 50% of the time was 70.4% compared to only a 30.5% probability for data set 1 (100% synthetic images) and a 40.1% probability for data set 3 (50% synthetic, 50% real). The improved classification performance in data set 1 could be due to a tendency of readers to label images as "real" slightly more often than "synthetic" (54% of the time compared to 46% of the time based on the data for the four readers used in the modeling).

TABLE 1

| | Pathologist 1 | | | Pathologist 2 | | | Pathologist 3 | | | Image Analyst 1 | | | Image Analyst 2 | | | Image Analyst 3 | | |
|---|---|---|---|---|---|---|---|---|---|---|---|---|---|---|---|---|---|---|
| | TP | TN | TP + TN | TP | TN | TP + TN | TP | TN | TP + TN | TP | TN | TN + TP | TP | TN | TN + TP | TP | TN | TN + TP |
| Dataset1 (10 synthetic) | 2 | 0 | 2 | 6 | 0 | 6 | 6 | 0 | 6 | 4 | 0 | 4 | 10 | 0 | 10 | 4 | 0 | 4 |
| Dataset2 (10 real) | 0 | 6 | 6 | 0 | 6 | 6 | 0 | 4 | 4 | 0 | 5 | 5 | 0 | 1 | 0 | 0 | 6 | 6 |
| Dataset3 (5 synthetic, 5 real) | 0 | 2 | 2 | 4 | 2 | 6 | 2 | 3 | 5 | 2 | 3 | 5 | 3 | 1 | 4 | 3 | 3 | 6 |
| Accuracy | | 33.3% | | | 60.0% | | | 50.0% | | | 46.7% | | | 46.7% | | | 53.3% | |

Experts' discrimination performance on synthetic/real images. TP represents the number of correctly identified synthetic images and TN represents the number of correctly identified real images.

Figure 8:
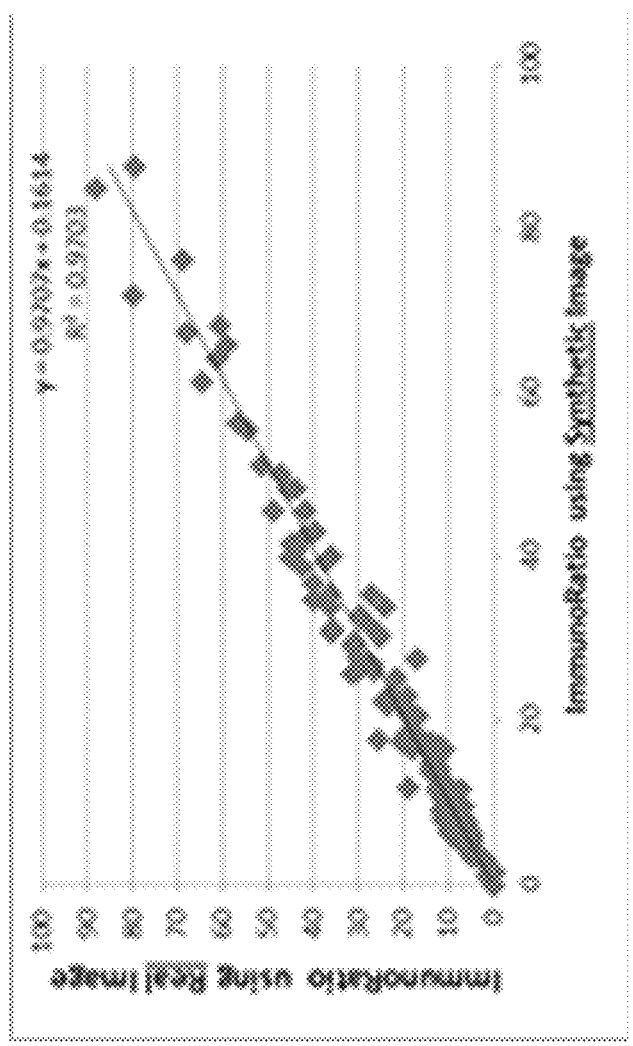
FIG. 8 is a graph illustrating the mean and standard deviation of the ImmunoRatio differences between real and synthetic images.
Figures 9A, 9B, 9C, 9D, 9E, 9F, 9G, 9H:
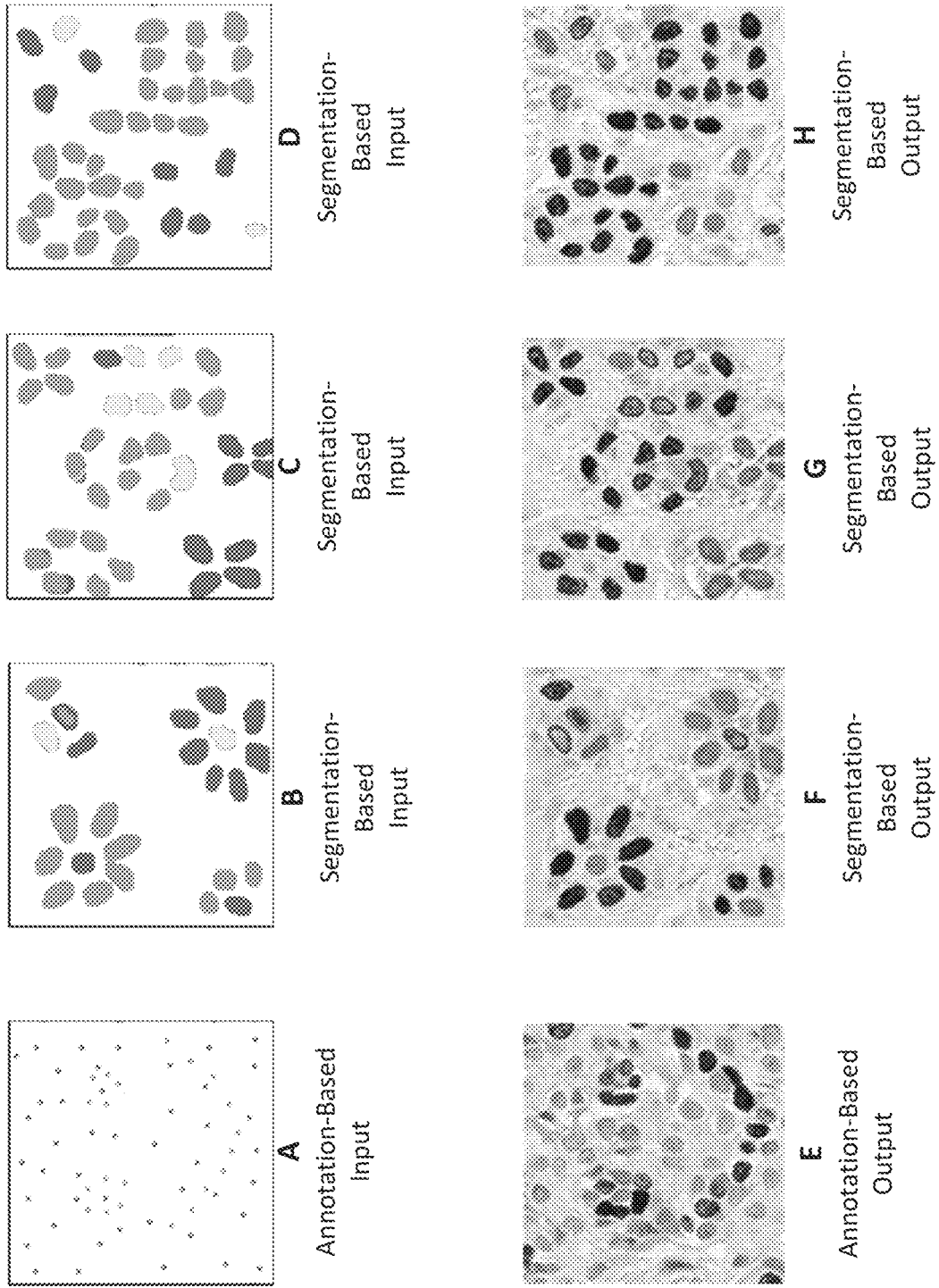
FIGS. 9A-9H illustrate generated synthetic images with different characteristics.

When the real and synthetic images are analyzed using computerized quantitative methods, it was observed that the mean and standard deviation of the ImmunoRatio differences between real and synthetic images are 2.55 and 2.25, respectively. The detailed information is given in FIG. 8.

During the experiments, it was observed that both approaches (i.e. location or segmentation initiated) allow us to create realistic phantom images. Although the accuracy of the segmentation approach was not perfect, leading to some under- and over-segmentation problems, the proposed method was robust to handle these challenges. On the other hand, in addition the location of the nuclei, the segmentation based approach allowed to define the size, orientation and shape information, as shown in the fully synthetic images of FIGS. 9A-9H.

CONCLUSIONS

In the described study, conditional Generative Adversarial Networks were used to create realistic looking histopathological cancer images with IHC staining. The disclosed method is different from the prior approaches to the problem in that at least the resulting synthetic images were observed to be realistic and hard to distinguish from their real counter parts even by experienced pathologists. For training, two different input methods were used: manual nuclei location annotations and segmentation masks generated by our algorithm. It was observed that using the segmentation masks may provide advantages over manual annotation. First, it allows defining shape, size and orientation information for each nucleus. Second, unequivocal staining conditions (i.e. a cell that cannot be easily labeled as positive or negative)

can be simulated with this approach (e.g. yellow 706 color regions in FIG. 7E). Finally, no manual annotation is needed if there is an existing segmentation algorithm.

This study has several practical implications. The artificially created datasets with known ground truth allows researchers to analyze the accuracy, precision, and intra- and inter-observer variability in a systematic manner and compare the human readers with a computer analysis. Besides, this approach may help algorithm developers for not only evaluating their methods but also for generating unlimited training and testing samples for algorithm development.

At the moment, each laboratory within the United States uses locally devised tissue slide preparation and scanning protocols. The study is significant as it has the potential to assist in careful selection of technical parameters that directly affect the tissue slide preparation and its display and also assist in regular checking of scanner performance with measurement of physical image parameters. Both, the technical parameters and the physical parameters have the potential to bring standardization to digital slide preparation process. Moreover, the study can assist in devising new standards to compare the quality of different scanners.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby fully incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method of generating a synthetic immunohistochemistry (IHC) stained digital slide having known values for one or more parameters, comprising:
   receiving, by a computing device, one or more inputs related to a desired synthetic slide mimicking an IHC stained tissue; and
   providing at least a portion of the one or more inputs to a generator, G, executing on the computing device, wherein the generator creates an output image corresponding to at least a portion of the one or more inputs related to the desired synthetic slide,
   wherein the output image comprises the synthetic IHC stained digital slide.

2. The method of claim 1, further comprising:
   performing an analysis of the synthetic IHC stained digital slide using an analysis method, wherein the analysis comprises determining an analyzed value for at least one of the one or more parameters; and
   comparing the analyzed value for the at least one of the one or more parameters to the known value for the at least one of the one or more parameters, wherein the comparison is used to evaluate the analysis method.

3. The method of claim 2, wherein the analysis method is a method for counting IHC-stained positive cells and IHC-stained negative cells.

4. The method of claim 3, wherein the method for counting IHC-stained positive cells and IHC-stained negative cells is performed manually.

5. The method of claim 3, wherein the method for counting IHC-stained positive cells and IHC-stained negative cells is performed automatically.

6. The method of claim 5, wherein the method for counting IHC-stained positive cells and IHC-stained negative cells is performed automatically using software.

7. The method of claim 1, wherein generating the synthetic IHC stained digital slide having known values for one or more parameters further comprises:
   analyzing, by a discriminator, D, executing on the computing device, the output image, wherein the discriminator either accepts or rejects the output image based on the analysis and wherein the discriminator uses artificial neural network (ANN) programming to analyze the output image,
   wherein if the output image is rejected by the discriminator, then another output image is created by the generator, and
   wherein if the output image is accepted by the discriminator, then the synthetic IHC stained digital slide is created.

8. The method of claim 7, wherein the one or more inputs include annotation or segmentation-based inputs.

9. The method of claim 7, wherein the one or more inputs include one or more of an image, a number or percentage of positive and negative cells, a location and/or size of positive and/or negative cells, or a description and/or location of artifacts that would be seen on a real slide.

10. The method of claim 7, wherein the ANN programming used by the discriminator comprises a convolutional neural network (CNN) based classifier.

11. The method of claim 10, wherein the CNN based classifier comprises patchGAN.

12. The method of claim 1, wherein the generator uses artificial neural network (ANN) programming to create the output image corresponding to the portion of the one or more inputs related to the desired synthetic slide.

13. The method of claim 12, wherein the ANN programming used by the generator comprises convolutional neural networks (CNN).

14. The method of claim 13, wherein the CNN comprises a modified version of U-net.

15. The method of claim 1, wherein the synthetic IHC stained digital slide is used as a ground truth to evaluate a method of analyzing IHC stained tissues.

* * * * *